United States Patent
Greene, Jr. et al.

(10) Patent No.: US 11,389,169 B2
(45) Date of Patent: Jul. 19, 2022

(54) TEMPORARY AORTIC OCCLUSION DEVICE

(71) Applicants: MicroVention, Inc., Tustin, CA (US); University of Virginia Patent Foundation, Charlottesville, VA (US); United States of America As Represented By The Secretary Of The Navy, Silver Spring, MD (US)

(72) Inventors: George R. Greene, Jr., Costa Mesa, CA (US); Ivan Sepetka, Los Altos, CA (US); Cathy Lei, Chino Hills, CA (US); Rupal Nguyen, Costa Mesa, CA (US); Matthew J. Bradley, Silver Spring, MD (US); Stephen T. Ahlers, Silver Spring, MD (US); Carl W. Goforth, Silver Spring, MD (US); James R. Stone, Charlottesville, VA (US)

(73) Assignees: Microvention, Inc., Tustin, CA (US); University of Virginia Patent Foundation, Charlottesville, VA (US); United States of America as Represented by the Secretary of the Navy, Silver Spring, MD (US)

( * ) Notice: Subject to any disclaimer, the term of this patent is extended or adjusted under 35 U.S.C. 154(b) by 390 days.

(21) Appl. No.: 16/289,485

(22) Filed: Feb. 28, 2019

(65) Prior Publication Data
US 2019/0192165 A1    Jun. 27, 2019

Related U.S. Application Data

(63) Continuation-in-part of application No. 15/690,152, filed on Aug. 29, 2017.
(Continued)

(51) Int. Cl.
  *A61B 17/12*  (2006.01)
  *A61B 90/00*  (2016.01)
  *A61B 17/00*  (2006.01)

(52) U.S. Cl.
  CPC .... *A61B 17/12109* (2013.01); *A61B 17/1204* (2013.01); *A61B 17/1214* (2013.01);
  (Continued)

(58) Field of Classification Search
  CPC .......... A61B 17/1204; A61B 17/12109; A61B 17/12136; A61B 17/12168;
  (Continued)

(56) References Cited

U.S. PATENT DOCUMENTS

| 5,935,139 A | 8/1999 | Bates |
| 6,589,264 B1 | 7/2003 | Barbut et al. |

(Continued)

FOREIGN PATENT DOCUMENTS

| EP | 3 010 563 | 4/2016 |
| WO | WO 96/40347 | 12/1996 |

(Continued)

OTHER PUBLICATIONS

WIPO, International Preliminary Examining Authority (U.S. Patent and Trademark Office), International Preliminary Report on Patentability dated Nov. 3, 2017 in International Patent Application No. PCT/US2017/049202, 7 pages.
(Continued)

*Primary Examiner* — Mohamed G Gabr
(74) *Attorney, Agent, or Firm* — Holland & Hart LLP

(57) ABSTRACT

A temporary aortic occlusion device is disclosed, having an expandable locator portion and an expandable occlusion portion. The expandable locator portion assists a user in determining whether the distal end of the device has been advanced within a patient's aorta, and the occlusion portion
(Continued)

is expanded to occlude the patient's aorta, preferably below the renal arteries.

19 Claims, 10 Drawing Sheets

Related U.S. Application Data

(60) Provisional application No. 62/382,705, filed on Sep. 1, 2016.

(52) U.S. Cl.
CPC .. *A61B 17/12136* (2013.01); *A61B 17/12172* (2013.01); *A61B 17/12177* (2013.01); *A61B 2017/00942* (2013.01); *A61B 2017/1205* (2013.01); *A61B 2090/0807* (2016.02)

(58) Field of Classification Search
CPC ........ A61B 17/12172; A61B 17/12177; A61B 2017/00115; A61B 2017/1205; A61B 2090/0807
See application file for complete search history.

(56) References Cited

U.S. PATENT DOCUMENTS

| | | |
|---|---|---|
| 7,278,430 B2 | 10/2007 | Kumar |
| 9,474,882 B2 | 10/2016 | Franklin |
| 2002/0161394 A1 | 10/2002 | Macoviak et al. |
| 2003/0135257 A1 | 7/2003 | Taheri |
| 2004/0006370 A1 | 1/2004 | Tsugita |
| 2004/0064092 A1 | 4/2004 | Tsugita et al. |
| 2005/0177182 A1* | 8/2005 | Van .................. A61F 2/01 606/157 |
| 2006/0058833 A1 | 3/2006 | VanCamp et al. |
| 2006/0135985 A1 | 6/2006 | Cox et al. |
| 2006/0200074 A1 | 9/2006 | Zadno-Azizi |
| 2007/0167980 A1 | 7/2007 | Figulla et al. |
| 2007/0173918 A1* | 7/2007 | Dreher ............... A61F 2/958 623/1.11 |
| 2007/0265656 A1 | 11/2007 | Amplatz et al. |
| 2010/0114017 A1 | 5/2010 | Lenker et al. |
| 2011/0172697 A1 | 7/2011 | Jönsson |
| 2012/0109057 A1 | 5/2012 | Krolik et al. |
| 2013/0096499 A1 | 4/2013 | Tchirikov |
| 2014/0121674 A1 | 5/2014 | Staunton |
| 2014/0214067 A1 | 7/2014 | Sachar |
| 2014/0257361 A1 | 9/2014 | Prom |
| 2014/0336690 A1 | 11/2014 | Zhadkevich |
| 2015/0005808 A1 | 1/2015 | Chouinard et al. |
| 2016/0015397 A1 | 1/2016 | Figulla et al. |
| 2018/0055515 A1 | 3/2018 | Greene, Jr. et al. |

FOREIGN PATENT DOCUMENTS

| | | |
|---|---|---|
| WO | WO 2014/134215 A1 | 9/2014 |
| WO | WO 2014/203078 A2 | 12/2014 |
| WO | WO 2014/203078 A3 | 12/2014 |
| WO | WO 2014/203078 A8 | 12/2014 |

OTHER PUBLICATIONS

International Search Report and Written Opinion of the ISA D dated May 7, 2020 in International Patent Application No. PCT /US2020/ 020531,10 pages.

Extended European Search Report dated Apr. 8, 2020, issued in European Patent Application No. 17847403.7.

* cited by examiner

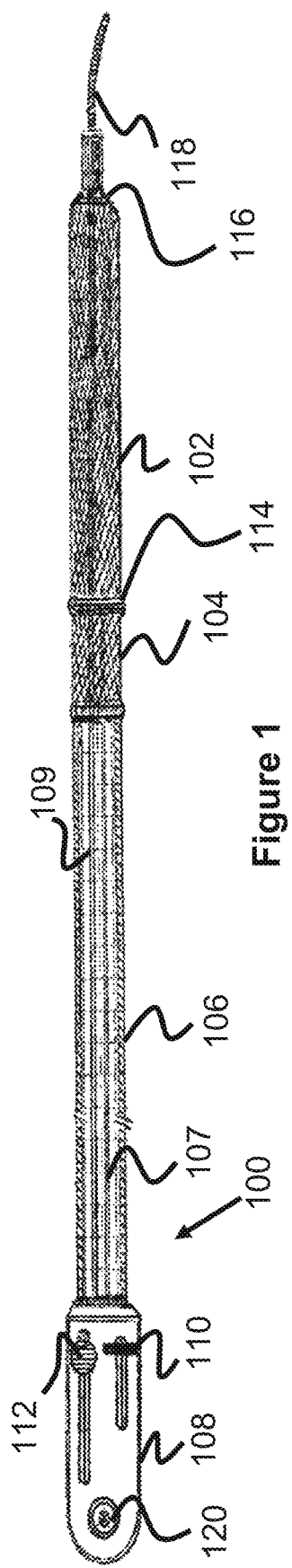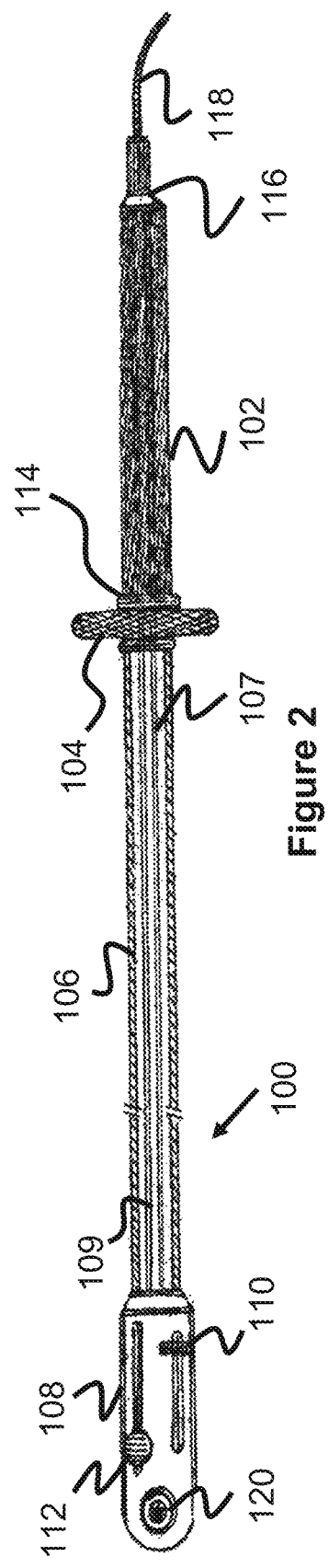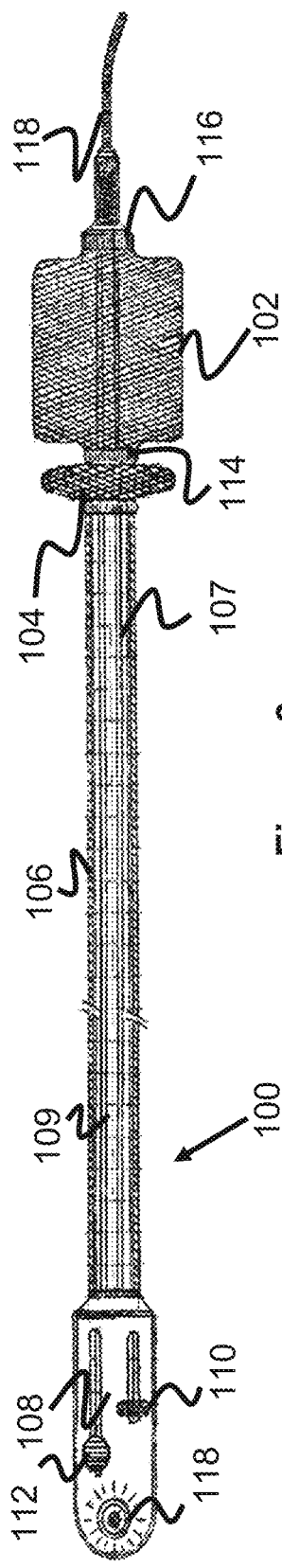

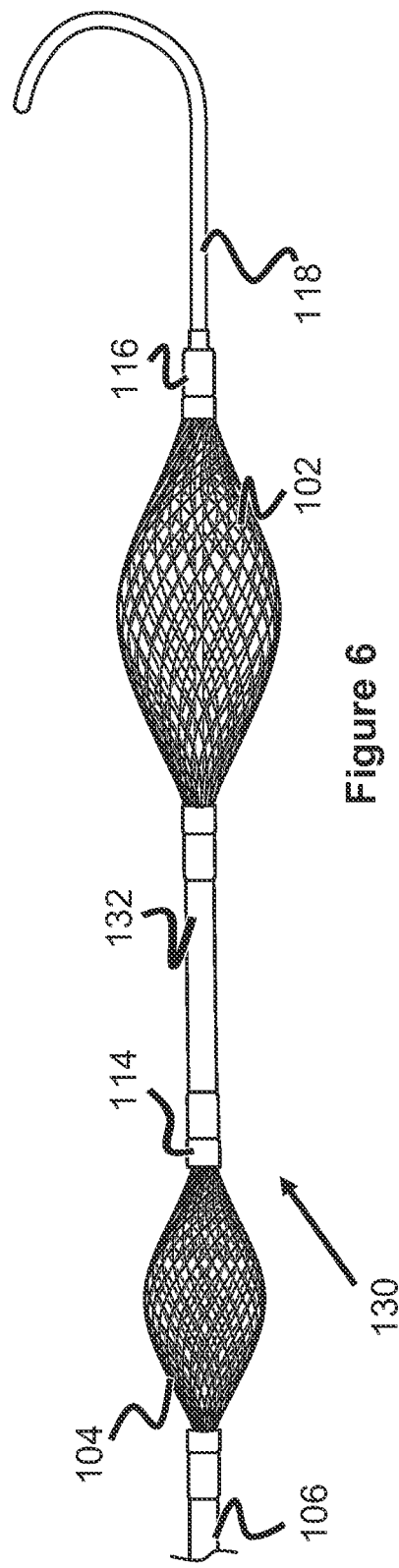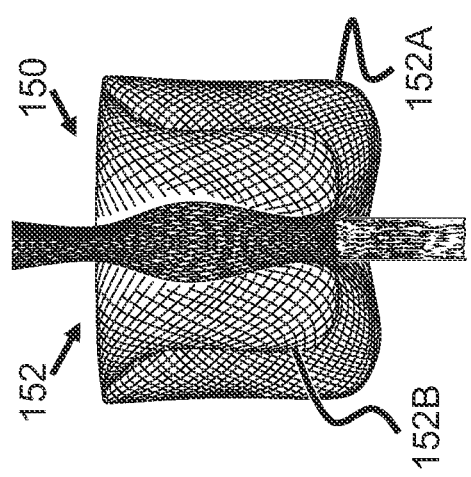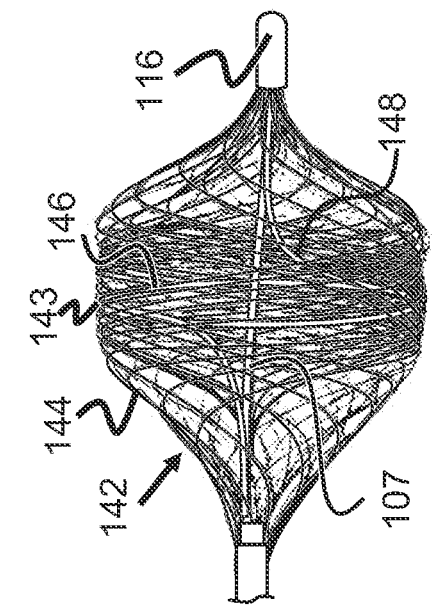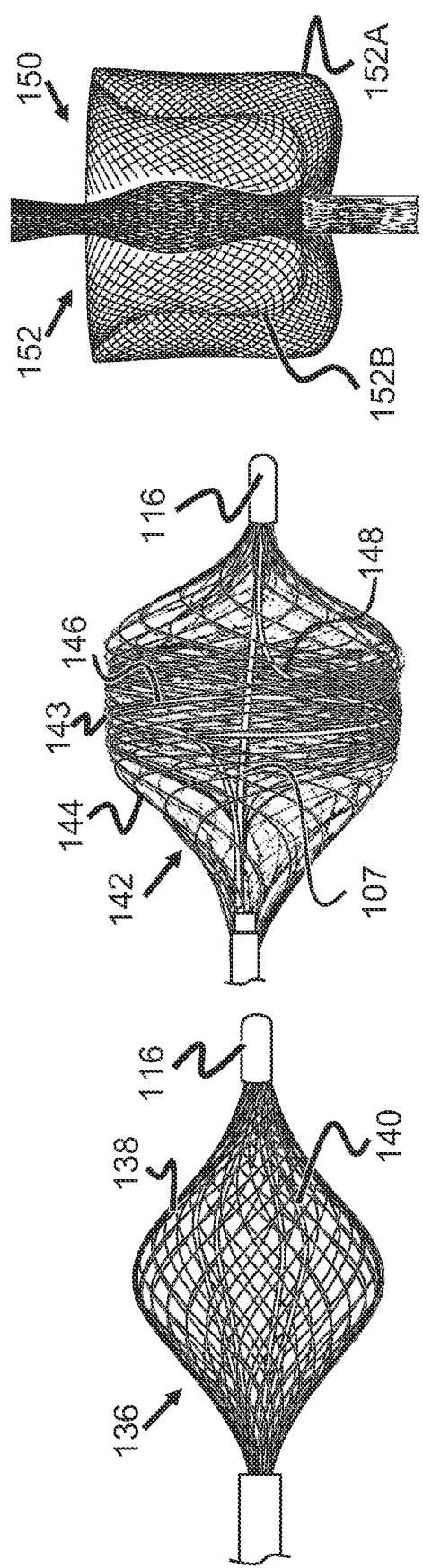

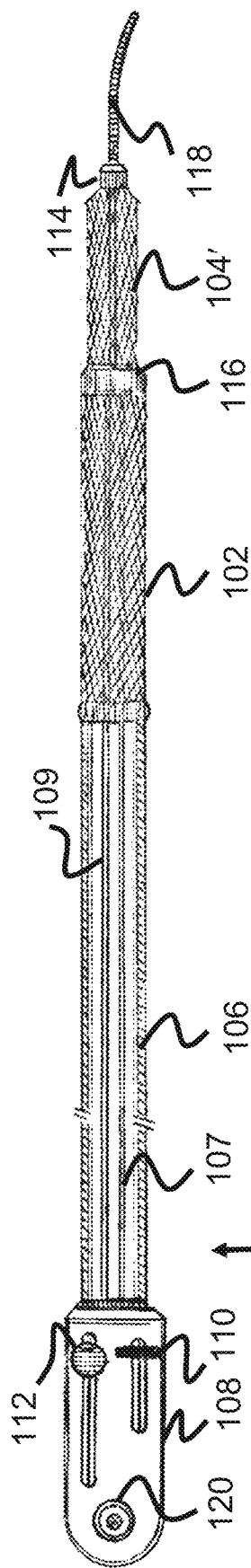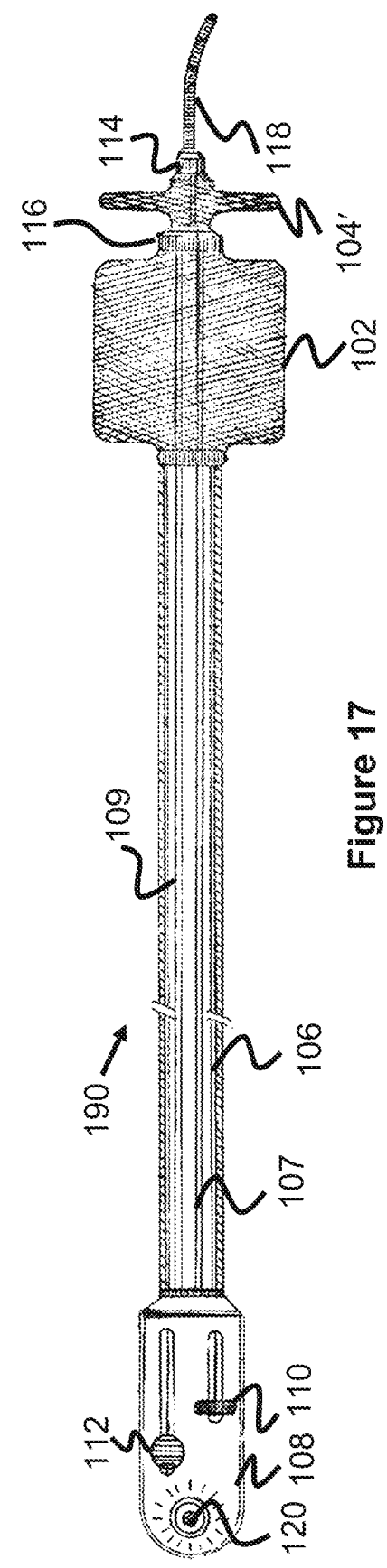
Figure 16
Figure 17

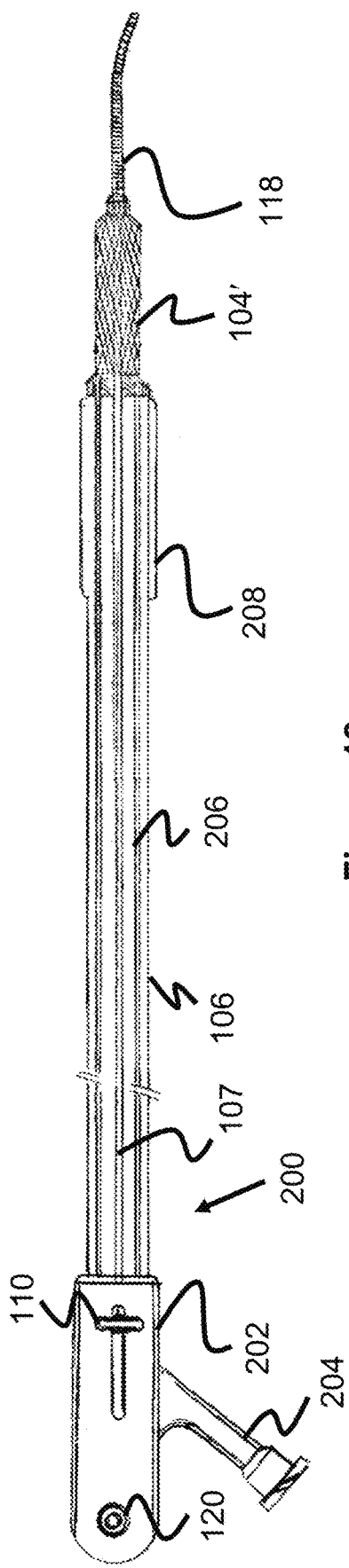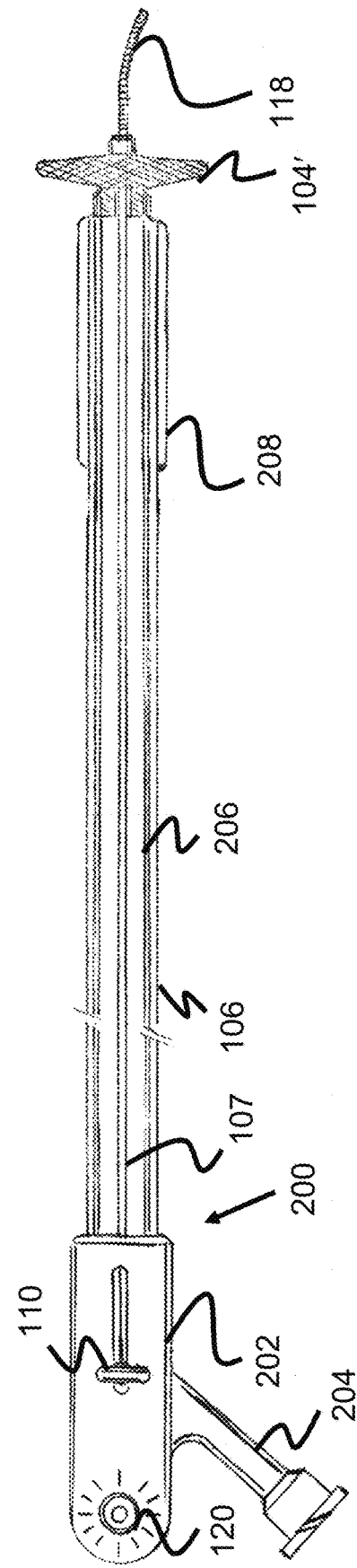

TEMPORARY AORTIC OCCLUSION DEVICE

RELATED APPLICATIONS

This application is a continuation-in-part of U.S. patent application Ser. No. 15/690,152 filed Aug. 29, 2017 entitled Temporary Aortic Occlusion Device, which claims priority to and benefit of U.S. Provisional Application Ser. No. 62/382,705 filed Sep. 1, 2016 entitled Temporary Aortic Occlusion Device, both of which are hereby incorporated herein by reference in their entireties.

BACKGROUND OF THE INVENTION

This application relates to a temporary aortic occlusion device for controlling torso hemorrhage.

Traumatic hemorrhage, primarily the result of blast injuries, is the leading cause of death in active-duty military service members. Although the widespread use of tourniquets has helped to reduce loss of life from severe lower extremity injury, non-compressible torso hemorrhage remains a challenge with high mortality given the relative anatomic inaccessibility of this region to obtain hemorrhage control.

Reports have suggested that up to 25% of hemorrhage sustained in the battlefield is potentially survivable with 50% the result of truncal trauma. Pelvic bleeding, in particular, can be severe and difficult to control, requiring advanced, upper echelon hospital-based care, such as angio-embolization, for definitive treatment. Because these advanced care methods and specially trained operators are at higher levels of care, mortality remains high. Unfortunately, outside of pelvic binders for pelvic fracture stabilization, which have limited success in hemorrhage control and are of no value in penetrating trauma there, has been little advancement in the control of non-compressible torso bleeding at the lower echelons of care.

Traditionally, early temporary control for non-compressible torso hemorrhage has been limited to thoracotomy with aortic cross-clamping. This technique has been reserved for moribund patients with absent or lost pulses and has an associated high morbidity and mortality. With growing interest in endovascular techniques for the management of vascular trauma the use of a resuscitative endovascular balloon occlusion of the aorta (REBOA) as an alternative to thoracotomy has been reported. For patients with massive pelvic or intra-abdominal hemorrhage who survive transport to an advanced care facility, placement of a temporary occlusion balloon in the infra-renal aorta, proximal to the aortic bifurcation, or the within the descending thoracic aorta have been used to provide time for more definitive treatment through surgical or endovascular methods. This in-hospital technique provides a method to stop flow of blood below the level of the balloon until the balloon can be deflated under controlled conditions. Insertion of an occlusive balloon is less invasive than a thoracotomy and can be placed in the unstable patient. Endovascular balloon occlusion has been shown to be lifesaving and superior to thoracotomy with aortic cross-clamping in civilian literature.

Placement of a temporary occlusion balloon in the aorta is performed under sterile conditions using ultrasound and fluoroscopic guidance, which requires time, skill, and bulky portable x-ray machines. Despite the potentially life-saving nature of aortic balloon occlusion in the setting of massive torso and/or pelvic hemorrhage, current approaches for the placement these devices require fluoroscopic guidance.

Fluoroscopy allows for: (i) intra-arterial injection of contrast dye to define the vascular anatomy, (ii) positioning of an aortic occlusion balloon with respect to this defined anatomy, and (iii) precise control of inflation of the device to allow for sufficient occlusion of the aorta while avoiding over-inflation that could result in rupture of the aorta secondary to balloon inflation.

A technique has been performed utilizing inflation of an aortic occlusion balloon in a trauma bay as a temporary measure for patients with massive pelvic hemorrhage and life-threatening shock, without fluoroscopic guidance. However, this approach requires the expertise of a senior Interventional Radiologist to interpret subtle tactile cues reflecting appropriate balloon placement and inflation. Further, this technique was performed in a "blind" fashion and relied upon the assumption of normal vascular anatomy. In spite of the reported success with balloon occlusion placement, positioning and confirmation has required valuable time, the use of fluoroscopic imaging, and skilled experienced practitioners at higher echelons of care. Additionally, due to the size of the currently available device surgery is required to repair the arteriotomy created by the catheter.

Any non-fluoroscopic approach for temporary occlusion of the aorta in the setting of hemorrhage should address: (i) positioning of the device with respect to individual patient anatomy, (ii) controlled inflation of the balloon or other occlusion device to account for varying aorta diameters, particularly in the under-resuscitated patient, (iii) a low profile, allowing for removal of the device without surgical repair, and (iv) must account for considerations related to the need for operator training in how to safely introduce the device into the femoral artery without creation of additional vascular injury.

Placement of a temporary aortic occlusion device may become an effective technique for hemorrhage control at lower echelons of care if it could be adapted for quicker, easier insertion by non-endovascular specialized providers. For example, Role II facilities such as the Navy Afloat Trauma System (NATS), the Navy/Marine Corps Forward Resuscitative Surgical Systems (FRSS), or Role I settings with Independent Duty Corpsmen and Navy Special Warfare SEAL corpsmen and physicians. Earlier availability of this technique could allow first-responders to stabilize non-compressible torso bleeding until advanced care was available resulting in decreased mortality.

The present invention addresses the need to improve forward surgical applications and targeted therapy for hemorrhagic injury.

SUMMARY OF THE INVENTION

The present invention is directed to a temporary aortic occlusion device having an expandable locator portion and an expandable occlusion portion. The expandable locator portion assists a user in determining whether the distal end of the device has been advanced within a patient's aorta, and the occlusion portion is expanded to occlude the patient's aorta, preferably below the renal arteries.

In one embodiment, the locator portion has a maximum expansion diameter that is smaller than a maximum expansion diameter of the occlusion portion. Additionally, the locator portion preferably has a maximum expansion diameter that is the same size or slightly smaller than the internal diameter of a patient's aorta, providing the user with little or no resistance to expansion when positioned in an aorta.

In one embodiment, the locator portion and the occlusion portion are each composed of a plurality of braided mesh wires. Both portions can be coated, laminated, or otherwise covered with a polymer.

In another embodiment, the occlusion portion can include multiple layers of braided wires. These layers can be created from discrete tubular mesh structures or a single, inverted, tubular mesh structure. In another embodiment, the occlusion portion can include an expandable disc structure, woven fabric, and/or spring-biased struts.

In one embodiment, the locator portion is located distal of the occlusion portion. In another embodiment, the locator portion is located proximal of the occlusion portion.

In another embodiment, the occlusion portion is a balloon that can be inflated with a fluid from a proximal end of the device.

The present invention is also directed to a method of temporarily occluding the aorta of a patient by inserting a temporary aortic occlusion device into a femoral sheath and towards the common iliac bifurcation. An actuation mechanism on the handle of the device is actuated to increase a diameter of a locator on a distal end of the device. If resistance is encountered with the locator, the device is advanced further until the locator can be increased in diameter without resistance. Next, an occluder on the distal end of the device is increased in diameter to occlude the patient's aorta.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which FIG. 1 is a temporary aortic occlusion device according to one embodiment of the present invention utilizing a proximal locator portion and a distal occlusion portion.

FIG. 2 is the temporary aortic occlusion device according to FIG. 1 where the proximal locator portion is in a radially expanded configuration.

FIG. 3 is the temporary aortic occlusion device according to FIG. 1 where both the proximal locator portion and the distal occlusion portion are in radially expanded configurations.

FIG. 6 is a temporary aortic occlusion device according to another embodiment of the present invention.

FIG. 7 is a temporary aortic occlusion device occlusion portion according to one embodiment of the present invention.

FIG. 8 is a temporary aortic occlusion device occlusion portion according to another embodiment of the present invention.

FIG. 9 is a temporary aortic occlusion device occlusion portion according to another embodiment of the present invention.

FIG. 16 is a temporary aortic occlusion device according to one embodiment of the present invention utilizing a distal locator portion and a proximal occlusion portion.

FIG. 17 is the temporary aortic occlusion device according to FIG. 16 where both the occlusion portion and the locator portion are in radially expanded configurations.

FIG. 18 is a temporary aortic occlusion device according to one embodiment of the present invention utilizing a proximal balloon and a distal locator portion.

FIG. 19 is the temporary aortic occlusion device according to FIG. 18 where the locator portion is in a radially expanded configuration.

DESCRIPTION OF EMBODIMENTS

Figure 4:
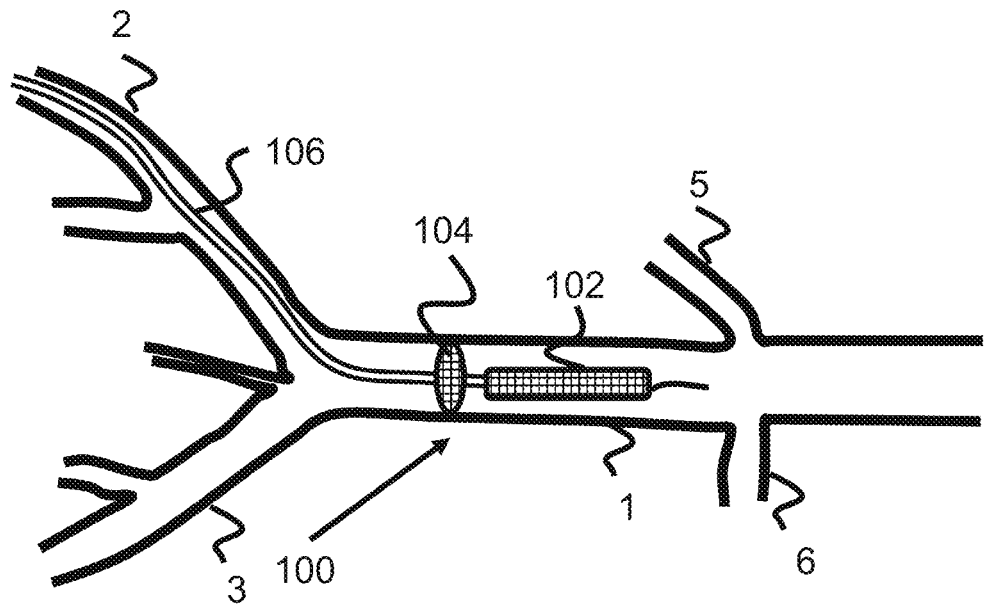
FIG. 4 is the temporary aortic occlusion device according to FIG. 2 in a blood vessel.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIGS. 1-5 are directed to a temporary aortic occlusion device 100 that has a radially expandable mesh locator 104 and a radially expandable mesh occlusion portion 102. The device 100 can be loaded in a femoral sheath (e.g., 6F Sheath) and advanced into the common iliac towards the aortic bifurcation target. Once the distal end of the device 100 is close to the target, the mesh locator 104 can be expanded and, if no resistance to the locator 104 occurs, the mesh occlusion portion 102 can be expanded to occlude the aorta.

The locator 104 is preferably composed of a wire mesh (e.g., 0.0005"-0.004" Nitinol wires) braided into a generally tubular shape. A proximal end of the locator 104 is fixed to distal end of a kink-resistant catheter tube 106 and a distal end of the locator 104 is fixed to ring 114, which is also connected to control wire 109. The control wire 109 is positioned within the lumen of the catheter tube 106 and its proximal end is fixed to slider 112. Hence, as the slider 112 is moved proximally, the control wire 109 moves the ring 114 proximally towards the catheter tube 106, causing the locator 104 to expand. The fully expanded locator 104 can be one of many different sizes, each of which designed to have a maximum expansion that is equal to or smaller than the target aorta size (e.g., 18 mm to 25 mm). The mesh of the locator 104 also may include an elastic hydrophilic coating to prevent blood flow from entering the catheter tube 106.

The occlusion portion 102 functions in a similar manner as the locator 104, having a proximal end fixed to ring 114 and a distal end fixed to ring 116. The ring 116 is further connected to control wire 107, which is slidably positioned within the lumen of the catheter tube 106 and has a proximal end connected to slider 110. Hence, as the slider 110 is moved proximally, it causes the occlusion portion 102 to expand.

The occlusion portion 102 is composed of a wire mesh (e.g., (e.g., 0.0005"-0.004" Nitinol or PET wires) that are laminated, coated (e.g., dip coating), or have a film applied either on its inner surface, outer surface, or both. Coating materials include polyurethane or silicone, and film materials includes polyethylene, linear low-density polyethylene, polyethylene terephthalate, and Nitinol. In one specific example, each of the wires are first coated in a polymer coating (e.g., polyurethane or polyethylene), braided, and then the inner surface of the occlusion portion 102 is completely coated in a thin 10-15 micron film of the same or similar polymer coating. In another specific example, ePTFE is coated on the inner and outer surface of the occlusion portion 102, "sandwiching" its braid. The occlusion portion 102 optionally has a length greater than that of the locator 104, so as to create a sufficient seal with the patient's aorta.

Preferably, the locator 104 and the occlusion portion 102 are spaced to ensure that the occlusion portion 102 does not occlude the renal arteries leading to the kidneys. A preferred average spacing between the two is about 4.00 cm to about 4.50 cm from each other based on the aortic anatomy of a range of average humans. However, it may be desirable to increase this distance in some circumstances (e.g., large patients) or decrease this distance (e.g., young/small patients).

One aspect of the device 100 is that it allows a user to sense whether there is resistance to expanding the locator 104 or not. In this respect, the locator 104 preferably has a maximum diameter expansion that is either the same size as or slightly smaller than the patient's aorta diameter (e.g., 18 mm to 25 mm). This expansion limit can be limited by the length of movement of the slider 112, as well as the construction of the braid. In contrast, the occlusion portion 102 is configured to have a slightly larger maximum expansion diameter than the locator 104 and/or patient's aorta. This allows the occlusion portion 102 to properly engage the aorta and occlude blood flow. If the device 100 only included the occlusion portion 102 and not the locator 104, a user would encounter expansion resistance prior to entering the aorta, as well as in the aorta, which could cause user-confusion about the device's position. By including the locator 104 that will not substantially encounter resistance in the aorta, the user can have a much higher degree of confidence that the device has entered the aorta.

Since the occlusion portion 102 must be capable of expanding within an aorta 1 and applying a reasonably sufficient force again walls of the aorta 1, there is a risk of rupturing or dissecting the smaller vessels connected to the aorta 1 if expanded too soon. In that regard, the locator 104 can be configured to assist expansion only until encountering a predetermined resistance force and/or with a less forceful expansion force. In this regard, the locator 104 can be expanded with less risk of rupturing the smaller, aortic-adjacent vessels.

One way to achieve this reduced expansion force is to compose the locator 104 of relatively fewer braided wires that, when encountering small amounts of force tend to deform or at least provide less force on the vessels (e.g., 36.005" wires for the locator 104 vs. 48.005" wires for the occlusion portion 102). Additionally, as previously mentioned, the locator 104 can be coated or laminated with a polymer material similar to the occlusion portion 102, which can further create resistance to expansion. Providing a relatively thick coating can further disperse force from the wires of the locator 104, thereby further reducing risk of vessel rupture.

An alternate or additional mechanism includes adding a spring or elastic member between the end of the control wire 109 and the ring 114, such that when resistance is encountered by the locator 104, the spring or elastic expands. Alternately or additionally, the entire control wire 109 can be composed of an elastic material that tends to stretch when resistance is encountered by the locator 104. Optionally, similar mechanisms can be included with regard to the occlusion portion 102, though with the ability to apply somewhat greater force before attenuation.

The handle 108 of the device 100 may also include an indicator light 120 that illuminates when the locator 104 has fully expanded. The handle 108 may have a contact or switch that is triggered when the slider 112 is slid to its proximal-most position to thereby indicate that the aorta 1 has been reached by the device 100.

The distal end of the device 100 also includes an atraumatic tip 118 that is fixed to ring 116. In one example, the tip 118 is composed of a helically-wound wire or coil and is sufficiently flexible to avoid injuring the aorta 1 of a patient.

In operation, the device is loaded directly into a femoral sheath and pushed distally from the femoral artery and into the common iliac towards the common iliac artery bifurcation. Once the catheter tip is close to the target, the slider 112 can be used to slow expand the locator 104. If resistance occurs, the slider 112 can be pushed distally to collapse the locator 104 and the device can be further advanced distally. Once the slider 112 can open fully without resistance, the slider 112 activates the light 120. Finally, the slider 110 can be moved proximally to expand the occlusion portion 102, blocking or occluding the aorta.

Figure 5:
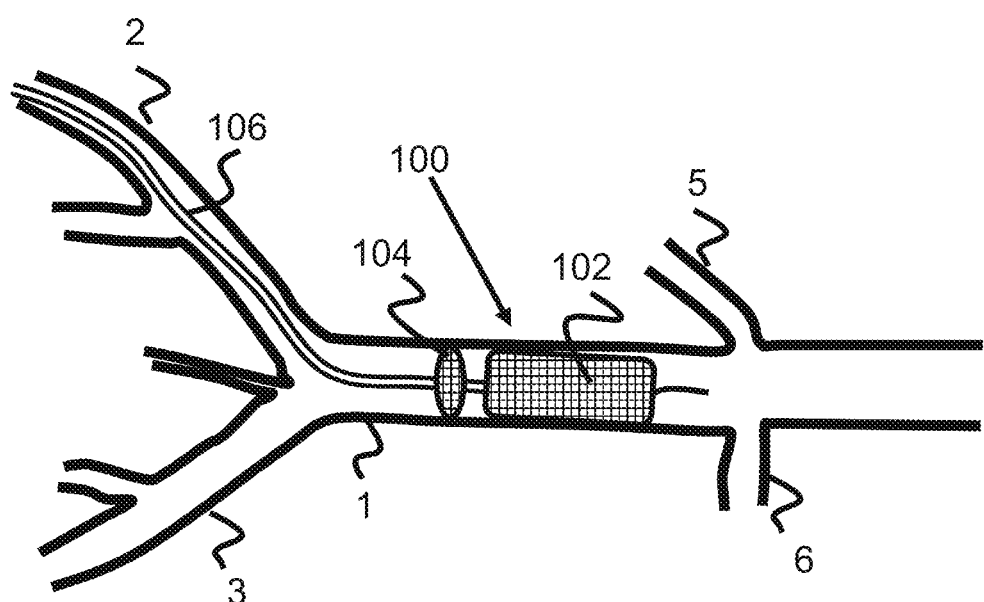
FIG. 5 is the temporary aortic occlusion device according to FIG. 3 in a blood vessel.
Figure 5A:
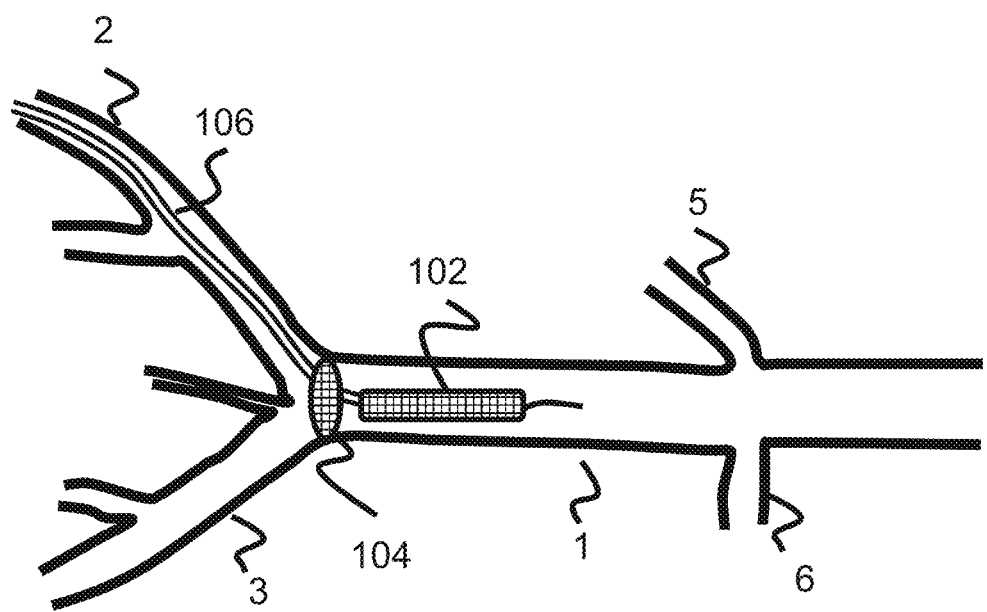
FIG. 5*a* is the temporary aortic occlusion device according to FIG. 2 in a blood vessel.
Figure 5B:
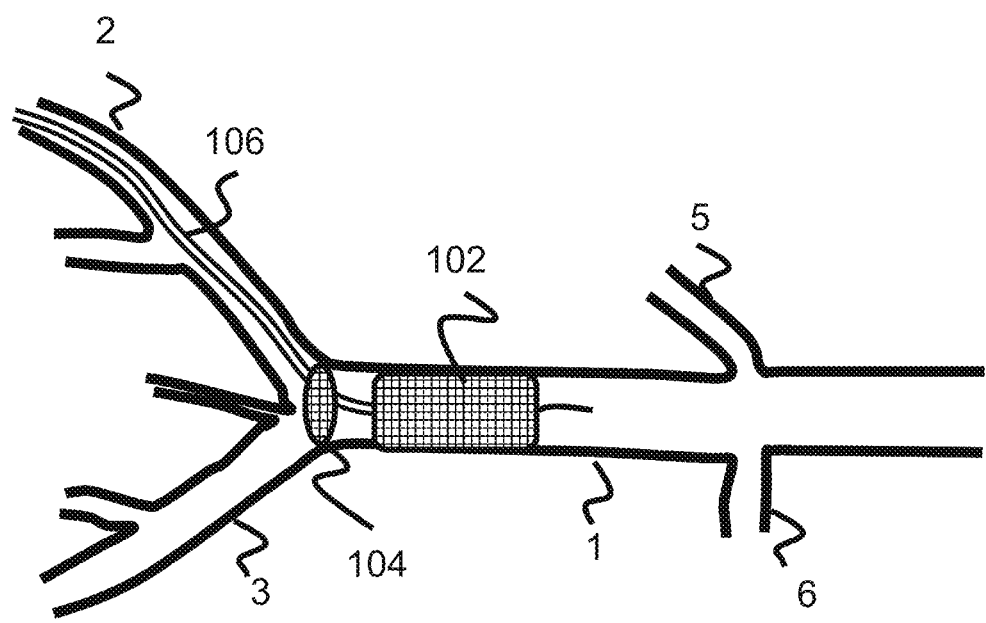
FIG. 5*b* is the temporary aortic occlusion device according to FIG. 3 in a blood vessel.

In some embodiments, it is beneficial to occlude the aorta at the base region of the aorta, near the bifurcation region between the larger aorta 1 and the smaller iliac branch vessels 2, 3 as shown in FIGS. 5a-5b. This junction corresponds to the pelvic region of the human body, as the iliac vessels lead to the upper leg region. For particular injuries, such as leg wounds, it is beneficial to occlude at this region to prevent blood from flowing past the occluder into the branch vessels which lead to the upper leg region (note that blood will flow through the heart, through the aorta, and then into the iliac arteries, and then the legs). When an indicator such as the one described in the paragraph above is used, the user would use the light (or other indication means, such as a sound) to confirm that the locator 104 connected to slider 112 can open fully without resistance. The user would then retract or proximally pull device 100 so that the locator as seated at the base of the aorta 1 adjacent iliac arteries 2, 3—at this point, the device 100 could no longer track proximally since the expanded locator 104 would contact the smaller iliac arteries, preventing further proximal movement. Occluder 102 is then expanded to occlude the aorta.

Alternatively, in situations where no light or other indicator is used, the user can rely on tactile feedback to locate the proper positioning. The user would track device 100 to a position within aorta 1, radially expand the locator 104, and retract the device until the locator 104 cannot be retracted any further—at this point, the locator 104 is now seated against the smaller iliac arteries 2, 3 preventing further proximal movement as shown in FIG. 5a. Occluder/occlusion portion 102 is then radially expanded to occlude the aorta. Locator 104 is further used as a location confirmation mechanism to determine that the device 100 is in the proper vessel, or confirm that the device is in a proper vessel or location. If the user is in the smaller iliac arteries rather than the larger aorta, then when the locator 104 is radially expanded, the locator will make quick contact with the vessel wall of the iliac, providing resistance and tactile indication that the user is not in the aorta. The user will radially collapse the locator and continue to deploy the device distally into the aorta, where confirmation of the location in the aorta is achieved when the locator 104 is expanded in the aorta and no resistance is met.

By way of example, aortas are typically sized from about 9 to 22 millimeters in diameter. The locator in its fully expanded state can be sized smaller than the aorta (for instance, locator 104 is sized 8 millimeters or less when fully radially expanded) so that no resistance/tactile feedback is encountered when the locator expands in the aorta. By way of example, occluder 102, in contrast, can be sized from about 9 to 30 millimeters in diameter when fully expanded in order to occlude the aorta. Note, since the occluder/occlusion portion 102 is meant to occlude the vessel (e.g., aorta), it is generally beneficial for the occlusion portion to have a maximum expansion diameter which is larger than the blood vessel diameter in order to effectively occlude the blood vessel. This fully expanded maximum expansion diameter represents the diameter that the occlusion portion 102 expands to in the absence of any resistance (e.g., when outside of the body, in absence of any constraints). When the occlusion portion 102 is expanded within the blood vessel, it cannot diametrically expand beyond the diameter of the vessel, though the ability to have a larger expansion diameter when unconstrained relative to the vessel size will help provide an effective seal against the vessel wall to help prevent blood from flowing beyond occluder/occlusion portion 102.

The user would deploy the device and radially expand the locator 104 to test the position of the device. In a smaller vessel, such as the common iliac arteries (these are the smaller arteries 2, 3 on the left side of FIGS. 4-5, which merge into the larger aorta 1), the locator 104 will radially expand and contact the walls of the smaller iliac vessel, causing the locator 104 to not expand fully and thereby indicating that the device is not in the aorta. Once the user feels this tactile sensation/tactile resistance, he or she can collapse the locator 104 and continue tracking it distally to approach the aorta. Once the locator 104 is in the aorta, since the vessel is oversized relative to the locator 104 and since the locator 104 when fully radially expanded is sized radially smaller than the aorta, the lack of resistance due to the locator not contacting the walls of the aorta would indicate that the locator 104 is now in the aorta.

The locator 104 offers several advantages as discussed above. Where occlusion at the base of the aorta (adjacent the iliac arteries) is desirable, then the locator 104 functions to confirm proper placement of the device by preventing proximal retraction of the device into the iliac arteries due to the expanded locator 104 being larger than the smaller iliac arteries. In this regard, the locator 104 also helps ensure that the device is not tracked too far distally in the aorta so as to occlude blood flow to the vital renal arteries 5, 6. The locator 104 also helps ensure that the device is located in the proper artery prior to the occlusion portion 102 being expanded.

Though the above disclosure and generally focuses on aortic occlusion, the device has particular utility for occluding blood flow at any vessel bifurcation region using the bifurcation seating method utilizing the locator element described above—such regions, by way of example, include the iliac/aortic junction in the pelvic region near the legs, the brachial/ulnar/radial arterial intersection in the arms, the common iliac/external iliac/internal iliac junction up in leg region, the popliteal/tibial arterial intersection near the knees. The occlusive device can be sized appropriately based on the region being treated, and a similar method described above is used where the occlusive device is seated in the larger parent artery and abuts against the smaller branch vessel. The locator 104 and occluder 102 can be appropriately sized up or sized down based on the blood vessels being treated.

In other example, the occlusion device can be used in a variety of vessels and not solely at bifurcation regions. For instance, most vessels have a particular size range profile. Additionally, many longer vessels are tapered over their length, such that the distal portion of the vessel (further away from the heart) is narrower than the portion of the vessel closer to the heart. In this way, the locator can be sized to fit a particular vessel or a particular portion of the vessel, where the user utilizes the locator to ensure proper positioning in a particular vessel. This can be based on the locator not contacting the vessel due to being undersized compared to the vessel (the lack of tactile feedback being used to ascertain placement in the proper vessel, as described above), or alternately being sized similarly or larger than the vessel, so that the user uses the tactile feedback of resistance as a marker to indicate that a proper occlusion position is reached. The locator concept, in other embodiments, can be used with a variety of other interventional procedures (such as embolic coil occlusion of aneurysms, other types of occlusion, or even other interventional procedures) where a locator is used along a catheter or along a device pusher assembly, and the user uses the locator to confirm that the device is in a proper treatment location prior to deploying the interventional device.

The device has particular utility in treating wounds where immediate blood stoppage is required, for instance to prevent bleed-out or as a first step before performing additional treatment. This can include, for instance, battle field injuries involving a leg or arm injury where an army medic would need to immediately use the device to limit blood flow to the wounded region. Another example is a paramedic/first responder function where an EMT/police officer/first responder is responding to a sudden event involving an arterial injury in the leg or arm region where immediate blood stoppage to an affected area is necessary. Similarly, this device can be used in a hospital or emergency room setting where an injured patient has an injury and the device is used to limit blood flow to the affected region as a first step in the treatment process. The device can be sized to fit various vessels/vessel sizes based on factors such as the associated vessel sizes of the particular treatment area, age of the patient, etc.

FIG. 6 illustrates another embodiment of an occlusion device 130 that is generally similar to the previously described device 100, however, the locator 104 is spaced apart from the occlusion portion 102 by tubular element 132. This embodiment may be useful if occlusion is desired at a higher location in the patient's aorta.

FIGS. 7-13 illustrate various alternate embodiments of the occlusion portion. For example, FIG. 7 illustrates an occlusion portion 136 braided from a plurality of wires 138 and having a plurality of wire struts 140 disposed within its cavity and connected to the control wire 107. The struts 140 are configured to provide a slight bias or spring-force to help urge the occlusion portion 136 to its expanded configuration. Specifically, the struts 140 can be metal wires connecting between the proximal and distal end of the occlusion portion 136 and that have a shape-memory configuration of a curve (e.g., a curve shape heat set into a shape memory alloy). In a compressed configuration, the struts 140 are relatively straight, but the shape-memory curve of the struts 140 provides an amount of force on the distal end of the occlusion portion 136 to assist the user in its expansion. Alternately, the struts 140 can be configured to return to a relatively straight configuration, biasing the occlusion portion 136 to its compressed configuration. While not shown, the occlusion portion 136 can be laminated, sealed, or otherwise coated in flexible layer of material, as described for other embodiments in this specification.

FIG. 8 illustrates another embodiment of an occlusion portion 142 that is composed of a plurality of braided wires 144. Within the braided wires 144 is a framework comprised of at least a proximal and distal support wires 148 connected to a circular support wire 143. The support wires 148 are connected to each end of the occlusion portion 142 so that, when expanded, the circular support wire 143 is positioned annularly around an axis of the occlusion portion 142. A polymer film 146 is connected to the circular support wire 143, generally forming a plane perpendicular to the axis of the occlusion portion 142. Since the circular support wire 143 and polymer film 146 is sized to expand to substantially the inner diameter of the inner cavity of the occlusion portion 142, an occlusive barrier is created. The braided wires 144 can be left bare or can include a coating, film, lamination, or other occlusive materials as described elsewhere in this specification.

FIG. 9 illustrates another embodiment of an occlusion portion 150 composed of a plurality of braided wires 152 that have a heat-set or memorized shape that causes the wires 152 to form an outer, cup shape 152A and an inner, inverted cup shape 152B. Put another way, the braided wires 152 invert to create two cylindrical layers. The braided wires 152 can be coated, laminated, covered with a film, or used with other occlusive materials as described elsewhere in this specification.

Figure 10:
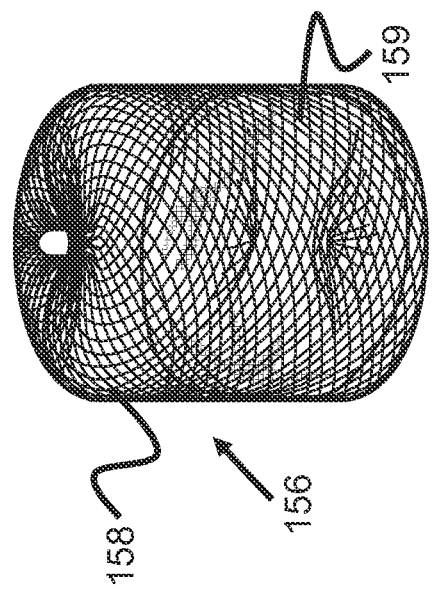
FIG. 10 is a temporary aortic occlusion device occlusion portion according to another embodiment of the present invention.

FIG. 10 illustrates yet another embodiment of an occlusion portion 156 having a generally cylindrical outer mesh layer 158 that surrounds an inner, cylindrical mesh layer 159. In one example, the outer mesh layer 158 is composed of relatively larger wires, while the inner layer 159 is composed of relatively smaller wires, which allows the inner layer 159 to have a lower porosity than the outer layer 158, since a greater amount of wires can be used (e.g., a higher pic-per-inch)—this would augment the occlusive effect of the occlusion portion by enhancing the resistance to blood flow once the blood permeates the outer layer. The outer and inner mesh layers 158, 159 can be each formed from a braided, mesh, tubular structure, or can alternately be formed from a single braided, tubular structure that is inverted to form the inner tubular layer 159. Either the outer layer 158, the inner layer 159, or both layers can be coated, laminated, covered with a film, or used with other occlusive material as described elsewhere in this specification.

Figure 11:
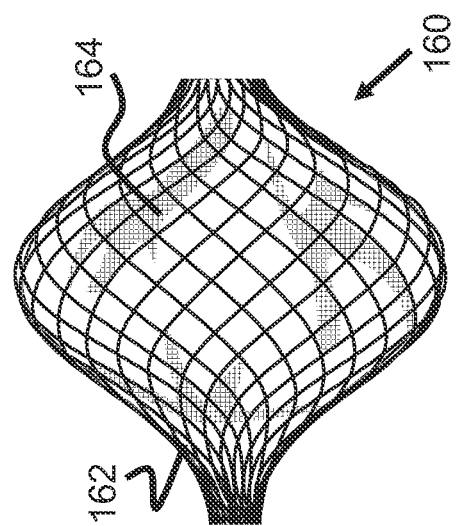
FIG. 11 is a temporary aortic occlusion device occlusion portion according to another embodiment of the present invention.

FIG. 11 illustrates another embodiment of an occlusion portion 160 having a plurality of braided wires forming a mesh layer 162, and an inner layer 164 composed of sealing, hydrophobic material such as polyurethane or silicone layer that is disposed within the mesh layer 162. Optionally, the inner layer 164 can be adhered or physically fastened to the outer mesh layer 162. Optionally, the outer surface of the mesh layer 162 can be coated, laminated, covered with a film, or used with other occlusive material as described elsewhere in this specification.

Figure 12:
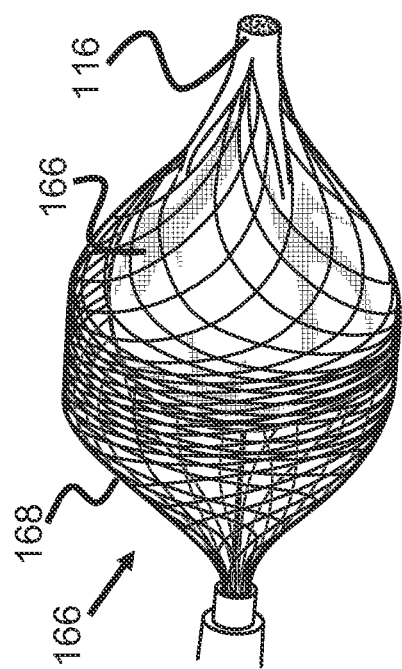
FIG. 12 is a temporary aortic occlusion device occlusion portion according to another embodiment of the present invention.

FIG. 12 illustrates another embodiment of an occlusion portion 166 having a plurality of braided wires forming a mesh layer 168, and an inner fabric material 166 fixed at a distal end of the occlusion portion 166. The inner fabric material 166 can be attached to locations around the circumference of the mesh layer 168, or can contain a wire support structure (similar to that formed by the support wires of FIG. 8) that expand the fabric material 166 when the occlusion portion 166 is expanded. The fabric material 166 can in only a proximal or distal half of the mesh layer 168, or can expand within the entire interior of the mesh layer 168. The fabric material 166 can form a funnel shape, a generally spherical shape, or similar shapes, depending on the interior shape of the mesh layer 168. The fabric material 166 can be formed from a woven fabric threads composed of a biocompatible material such as PET. Optionally, the outer surface of the mesh layer 168 can be coated, laminated, covered with a film, or used with other occlusive material as described elsewhere in this specification.

Figure 13:
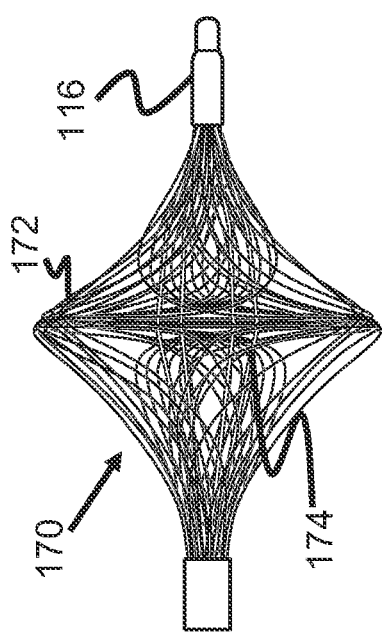
FIG. 13 is a temporary aortic occlusion device occlusion portion according to another embodiment of the present invention.

FIG. 13 illustrates another embodiment of an occlusion portion 170 which is generally similar to the embodiment of FIG. 7 in that it has a braided mesh layer 172 that has a plurality of wire struts 174 (e.g., 4) extending between its proximal and distal ends. The struts 174 are bias into a curved shape, such that they provide additional expansion force to the mesh layer 172. The mesh layer 174 forms a generally diamond shape or a shape of two cones connected together. Optionally, the outer surface of the mesh layer 168 can be coated, laminated, covered with a film, or used with other occlusive material as described elsewhere in this specification.

Figure 15:
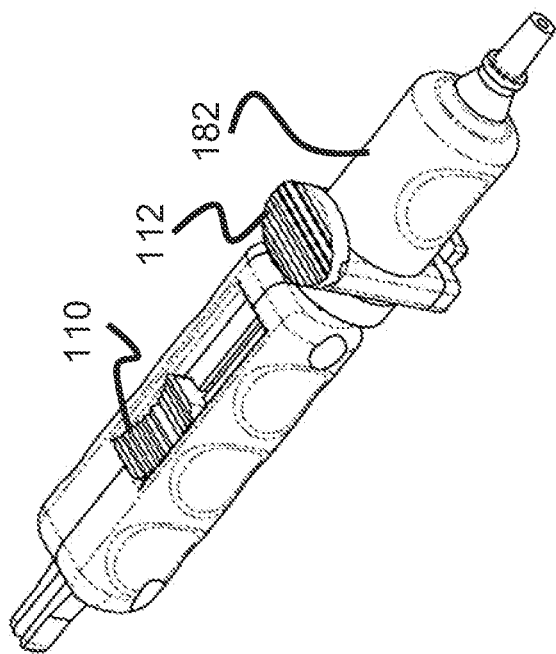
FIG. 15 is a temporary aortic occlusion device handle according to another embodiment of the present invention.
Figure 14:
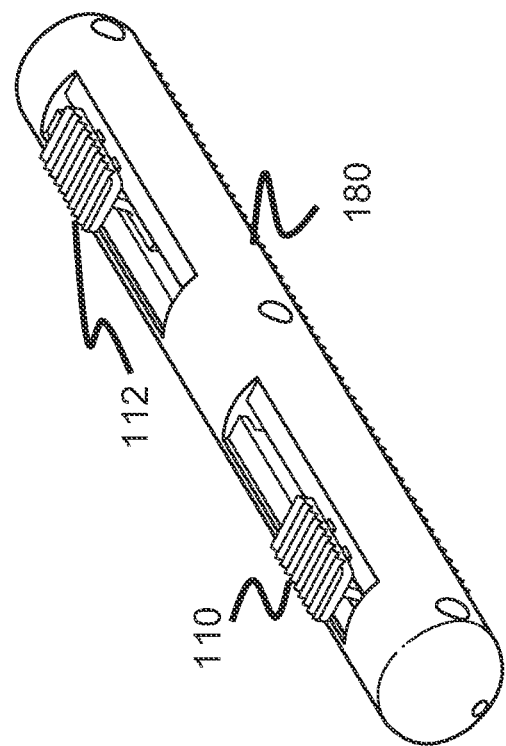
FIG. 14 is a temporary aortic occlusion device handle according to one embodiment of the present invention.

Turning to FIGS. 14 and 15, two different embodiments of handles (180, 182) are illustrated. These embodiments arrange the sliders 110, 112 in line with each other, instead of side-by-side, as in prior embodiments. Additionally, the handle 182 includes a slider 112 that is disposed entirely around the distal portion of the handle 182 and slides in a coaxial manner proximally and distally on the handle 182, the tracks are not shown but in such an embodiment slider 112 would have tracks that it slides on similar to the track that slider 110 slides on. In another embodiment, slider 112 could rotate in order to translate a connected wire—in this embodiment slider 112 would mate over the control wire in a ratcheting-type engagement where rotating slider 112 would translate the control wire which is connected to slider 112.

FIGS. 16 and 17 illustrate another embodiment of a temporary occlusion device 190 that is generally similar to the device 100 shown in FIGS. 1-5. However, the locator 104' is positioned distal of the occlusion portion 102.

Figure 20:
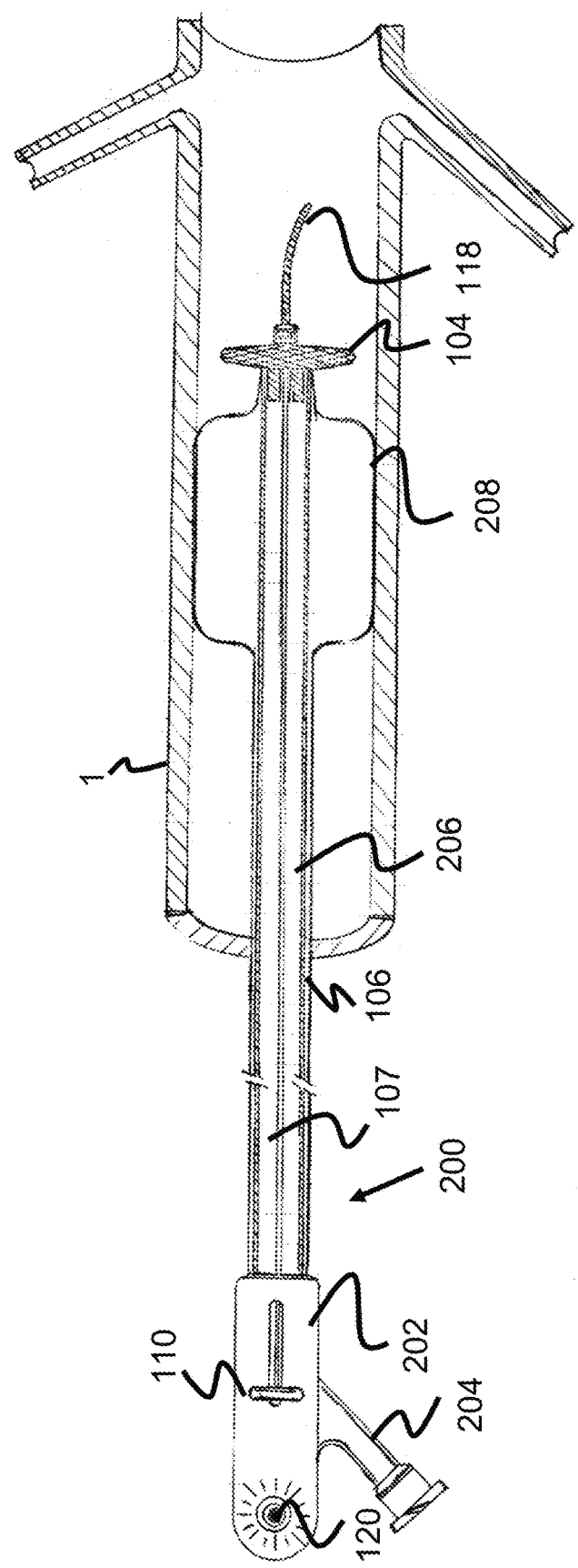
FIG. 20 is the temporary aortic occlusion device according to FIG. 18 in a blood vessel, where both the balloon and locator portions are in radially expanded configurations.

FIGS. 18-20 illustrate yet another embodiment of a temporary occlusion device 200 that is generally similar to the device 190 of FIGS. 16 and 17, including the distal location of the locator 104'. However, instead of a mesh-based occluding portion, a balloon 208 is fixed proximal of the locator 104' (alternately, the balloon 208 could be fixed distally of the locator 104). A fluid connection port is connected for a fluid source (e.g., a syringe of fluid) and is open to an interior passage 206 within the catheter tube 106, which ultimately connects to an interior of the balloon 208 to allow for selective inflation.

Preferably, the balloon 208 is composed of a highly compliant material. In this respect, if the balloon 208 is over inflated, it will elongate rather than continuing to apply radial force on the wall of the aorta, thereby avoiding balloon-induced aortic damage.

These balloon occluder concepts can also be used in the methods shown in FIGS. 4-5b and described above where the locator device is used to properly seat the occluder near the bifurcation region of an artery, and the balloon occluder is then used to occlude the vessel (e.g., aorta) to limit/prevent bloodflow further downstream beyond the occluder.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of occluding a trauma site endovascularly with an occlusive device having an elongated device body, a locator portion, and an occlusion portion comprising:
   pushing the elongated device body through a blood vessel;
   radially expanding the locator portion;
   confirming proper position of the occlusive device in the blood vessel using the locator portion; and
   radially expanding the occlusion portion to occlude the blood vessel, wherein confirming proper position of the occlusive device in the blood vessel comprises retracting the locator portion to a blood vessel region having a diameter that is smaller than or equal to a diameter of the locator portion such that the locator portion encounters resistance.

2. The method of claim 1, wherein the locator portion is composed of a plurality of braided wires.

3. The method of claim 1, wherein confirming proper position of the occlusive device in the blood vessel comprises the locator portion radially expanding without contacting the blood vessel.

4. The method of claim 1, wherein confirming proper position of the occlusive device in the blood vessel comprises retracting the locator portion to a bifurcation region.

5. The method of claim 1, wherein the locator portion radially expands to a first diameter, and the occlusion portion radially expands to a second diameter larger than the first diameter.

6. The method of claim 1, wherein the occlusion portion is composed of a plurality of braided wires.

7. The method of claim 1, wherein radially expanding the locator portion comprises moving a first slider on a proximal handle.

8. The method of claim 7, wherein radially expanding the occlusion portion comprises moving a second slider on a proximal handle.

9. The method of claim 1, wherein the occlusion portion is a balloon.

10. The method of claim 9, wherein the balloon is radially expanded by filling the balloon with an inflation media delivered through a proximal handle.

11. A method of occluding an aorta endovascularly with an occlusive device having an elongated device body, a locator portion, and an occlusion portion comprising:
    pushing the elongated device body through the aorta;
    radially expanding the locator portion;
    confirming proper position of the occlusive device in the aorta using the locator portion; and
    radially expanding the occlusion portion to occlude the aorta, wherein confirming proper position of the occlusive device in the blood vessel comprises retracting the locator portion to a blood vessel region having a diameter that is smaller than or equal to a diameter of the locator portion such that the locator portion encounters resistance.

12. The method of claim 11, wherein the locator portion is radially expandable to a diameter less than or equal to a diameter of the aorta.

13. The method of claim 11, wherein the occlusion portion is radially expandable to a diameter greater than or equal to a diameter of the aorta.

14. The method of claim 11, wherein confirming proper position of the occlusive device in the aorta further comprises proximally retracting the occlusive device while the locator portion is expanded so that the locator portion is seated adjacent to an iliac artery.

15. The method of claim 11, wherein the occlusive device further comprises a proximal handle which controls expansion of the occlusion portion and the locator portion.

16. A method of occluding a parent artery with an occlusive device having an elongated device body, a locator portion, and an occlusion portion comprising:
    pushing the elongate device body through a bifurcation region into the parent artery;
    radially expanding the locator portion;
    confirming proper position of the occlusive device in the parent artery using the locator portion; and
    radially expanding the occlusion portion to occlude the parent artery, wherein confirming proper position of the occlusive device in the blood vessel comprises retracting the locator portion to a blood vessel region having a diameter that is smaller than or equal to a diameter of the locator portion such that the locator portion encounters resistance.

17. The method of claim 16, wherein confirming proper position of the occlusive device in the parent artery includes tactile indication that the locator portion does not contact the parent artery when radially expanded.

18. The method of claim 16, wherein the parent vessel is an aorta and the vessel bifurcation region is an iliac-aorta bifurcation region.

19. The method of claim 16, wherein confirming proper position of the occlusive device in the parent artery comprises proximally retracting the occlusive device to a vessel bifurcation region adjacent the parent artery.

* * * * *